United States Patent [19]

Perrotta

[11] 4,213,044
[45] Jul. 15, 1980

[54] METHOD AND APPARATUS FOR DETERMINING OIL MIST IN COMPRESSED AIR

[75] Inventor: Kenneth A. Perrotta, Methuen, Mass.

[73] Assignee: Whatman Reeve Angel Limited, Maidstone, England

[21] Appl. No.: 970,246

[22] Filed: Dec. 18, 1978

[51] Int. Cl.² .................... G01T 1/167; G01T 1/169
[52] U.S. Cl. ............................................. 250/301
[58] Field of Search .............. 73/29; 250/301, 362, 250/365, 458, 459, 461

[56] References Cited

U.S. PATENT DOCUMENTS

| | | | |
|---|---|---|---|
| 2,297,939 | 10/1942 | Campbell | 250/301 |
| 3,614,433 | 10/1971 | Caldwell | 250/301 |
| 4,057,721 | 11/1977 | deVial et al. | 250/301 |

FOREIGN PATENT DOCUMENTS

2532869  2/1977  Fed. Rep. of Germany .......... 250/301

*Primary Examiner*—Bruce C. Anderson
*Attorney, Agent, or Firm*—Richard P. Crowley

[57] ABSTRACT

A test kit and method for determining in a semiquantitative manner the amount of oil mist in a compressed-air stream, which method comprises bleeding a small sample from the compressed-air stream containing oil mist whose concentration is to be determined; directly impinging the compressed-air stream so bled for a defined time period through a defined orifice onto the surface of a coated plate containing an ultraviolet radiation indicator to capture the oil-mist particles in the compressed-air stream, thereafter comparing the test plate with a standard plate of known concentration of oil mist under ultraviolet radiation to determine the degree of flourescent quenching as an indication of the amount of oil mist in the compressed-air stream.

21 Claims, 3 Drawing Figures

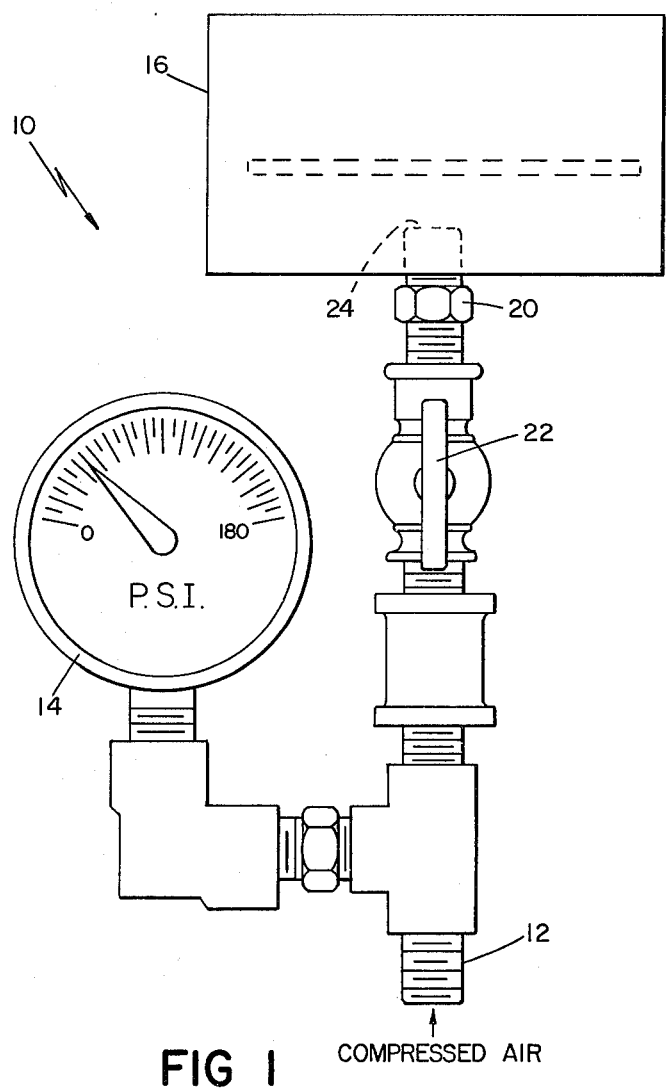
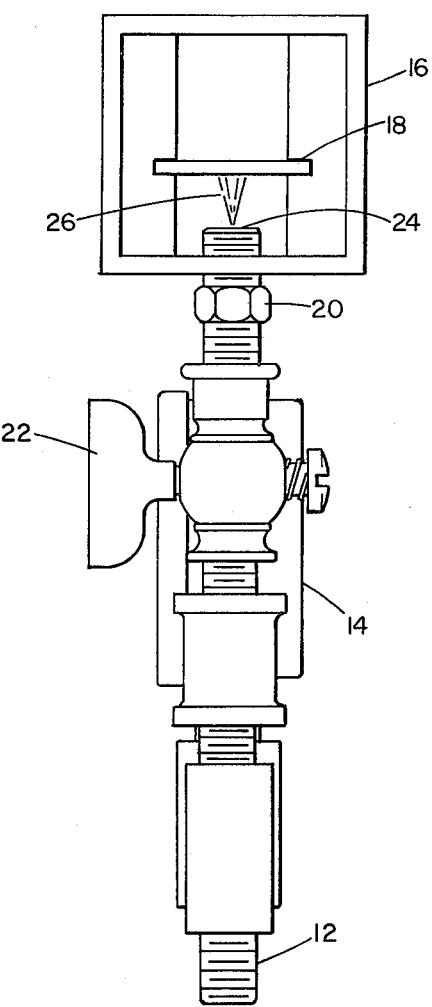
FIG 1  FIG 2
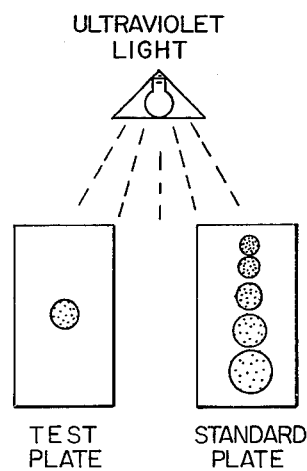
FIG 3

METHOD AND APPARATUS FOR DETERMINING OIL MIST IN COMPRESSED AIR

BACKGROUND OF THE INVENTION

Air compressors and vacuum pumps are typically oil sealed or lubricated and thus compressors and pumps generate a heavy concentration of oil both in the form of oil vapor and oil-mist particles in the exhaust air during the pumping cycles. Typically the oil-mist droplets are very small, often well below 5 microns in average size. The oil mist, which is mostly composed of finely divided liquid droplets dispersed in air and visible typically as a haze, a fog, and the droplet size represent a health hazard in the environmental working place. Typically such oil mist is removed by employing a suitable filter, such as a glass-fiber filter, which removes the oil mist by a process of coalescing that permits the coalesced oil to drain from the filter.

There is a need for a means of testing on an easy semiquantitative basis the amount of oil mist in compressed air in order to determine the type and nature of the filters to employ in the compressed-air line. Present techniques to determine the amount of oil mist in compressed air are often quite cumbersome, expensive, complex or tedious. Such present techniques include the sampling of air from the compressed-air line, which air sample is then subject to test by a gas chromatograph, a mass spectrometer or hydrocarbon analyzer to determine the amount of oil in the air. However, such techniques often measure not only the oil-mist particles captured by the glass-fiber filter, but also the oil vapor in the air and in addition such tests do not provide for the testing of the compressed air under operating-line conditions and pressure. Such test methods also represent problems in getting an accurate representative sample of the compressed air, particularly where the oil-mist particles are so small and therefore, there are problems associated with the isokinetic sampling of compressed air.

One test method in use is a modification of a DRAEGER tube wherein a glass tube is filled with a selective oil absorbent and the gas to be tested is then passed through the tube. The absorbent contains a visual color indicator and the change in color and the intensity of the color change are observed as an indication of the presence of a particular gas. This test is typically employed for toxic gases, such as hydrogen sulfide, rather than for oil mist from compressed air or vacuum pumps. In the test modification oil absorbent with a color indicator is employed in a tube and compressed air bled through the tube at a known flow rate and the color change observed as an indication of oil mist in the air. This test is still quite insensitive, since the amount of air flow depends on the line pressure and the time factor involved in the test. In summary the present mentods and related techniques to determine oil-mist particles in a compressed-air stream are quite limited, insensitive, complex, expensive, tedious, hard to perform and unsatisfactory.

SUMMARY OF THE INVENTION

My invention relates to a method of and a kit apparatus for the determination of oil mist or suspended-oil particles in compressed-air streams and the standard plates used therein. In particular my invention relates to a direct, semiquantitative test method and technique wherein the amount of oil mist in a compressed-air stream can be determined by comparison of test means with a set of standards whereby the amount of oil mist in the compressed air may be determined.

My test method comprises in general the sampling, such as by bleeding, of the compressed-air stream containing the oil mist whose concentration is to be determined from the compressed-air source or line to be tested through a defined orifice, directly impinging the compressed-air streams so bled for a defined time period onto a coated plate containing a UV radiation fluorescent material, which plate captures at least a portion of the oil-mist particles in the compressed-air stream impinging on the plate surface, and then comparing the test plate under UV radiation with a standard plate to determine by the degree of fluorescent quenching between the test plate and the standard plate the amount of oil mist present in the tested compressed-air stream.

For example, my method comprises bleeding a compressed-air stream through a known orifice, for example, a 0.010" orifice, in a pipe plug with a fitting in the air line, which directs the bleeded compressed-air jet against the flat surface of a coated microscope glass slide with the slide coated with an active material which fluoresces under radiation, such as a slide coated with silica and a UV fluorescent indicator. Such glass-covered slides are commonly employed in thin-layer liquid chromatography, although not for the purposes of this invention. The glass slide is permitted to become covered with oil over a defined time period, for example, from 10 seconds to 30 minutes, more typically for example 30 seconds to 10 minutes, with the compressed-air line pressure often ranging from 80–125 psig.

The test slide then coated with the impinged oil-mist particles is then removed and placed in a UV radiation box together with a standard test slide and both subjected to ultraviolet radiation and the amount of fluorescent quenching of the test slide compared with the fluorescent quenching of the standard slide is visually observed to determine the amount of oil-mist particles in the tested compressed air either by the area of the nonfluorescing spot or in the lower concentration of oil by visually observing a difference in the degree of darkness of the spot.

A standard test slide is separately prepared and distributed and illustrates the amount of fluorescent quenching on the test slide for varying degrees of known concentration of oil mist. The test slide is calibrated in relation to the percent oil or parts per million of oil mist. The oil mist on the test slide absorbs the UV radiation and quenches the fluorescence of the indicator on the plate. The amount of quenching of the fluorescent indicator is an indication of the percent of oil in the compressed air over the defined time period. The standard slide contains a series of spots or other forms of different diameters and/or intensity corresponding to different amounts of quenching due to the presence of different amounts of oil in a compressed-air stream composed during the same time over roughly the same pressure through the same defined orifice. This test procedure is simple, direct, easy and semiquantitative enough to permit a determination of the correct filters to be employed in the compressed-air line.

My apparatus also comprises a test kit or assembly for use in determining the amount of oil mist in compressed air, which kit comprises in combination a standard fitting for insertion in the compressed-air line of an air compressor or vacuum pump or other pressurized air source, which fitting contains the defined orifice, for example, from 0.010" to 0.020" in diameter; a holder for a test plate, the holder adapted to be placed adjacent to and opposite the orifice so that the sample bleeded air stream from the orifice will impinge on one surface of the test plate; a test plate which is adapted to be inserted into the holder and which contains a coating on at least one side thereof (preferably both sides) which absorbs or retains oil-mist particles and which coating also includes a UV fluorescent indicator compound; a standard test plate which contains oil at defined concentration ranges on the plate; and an UV radiation fluorescent test chamber adapted to permit the insertion of a test and a standard slide side by side or in a comparison manner and a source of ultraviolet radiation on the surfaces of each slide. The tester views the test slide together in the UV radiation chamber with the standard slide and determines the amount of quenching which is proportional to the amount of oil-mist in the tested compressed-air line. By a comparison of the amount of quenching of the test plate and the standard plate the tester determines the amount of oil mist in the compressed air.

For the purposes of illustration only my test method and apparatus will be described in connection with the preferred embodiment and in connection with the determination of oil mist in a compressed-air line. However, it is recognized that various changes and modifications may be made in the described method and apparatus by those persons skilled in the art, all within the spirit and scope of my invention.

BRIEF DESCRIPTION OF THE DRAWING

FIG. 1 is a front plan view of the test kit apparatus.
FIG. 2 is a scale plan view of the apparatus of FIG. 1.
FIG. 3 is a schematic illustration of the comparison between standard and test plates in determining the amount of oil mist vapor.

DESCRIPTION OF THE PREFERRED EMBODIMENT

Referring in particular to FIGS. 1 and 2 there is shown a test apparatus 10 of my invention which comprises the test apparatus to be installed on a compressed-air line whose compressed air is to be tested for oil-mist concentration with the test apparatus installed through the NPT threaded Nipple 12. The test apparatus includes a pressure gauge 14, a slide holder 16, and a slide 18 mounted essentially perpendicular and spaced a short defined distance about 1" from a fitting 20 containing a defined orifice 24, for example, 0.010 inches, through which air is admitted through the employment of a valve 22 so that the air sample 26 impinges on the surface of plate 18. Test holder 16 is a piece of aluminum square tubing to form a box-like shape with aluminum ridges on each side with a groove in each edge to support a test plate inserted in the groove.

In operation the apparatus test kit 10 is installed on a compressed-air line and a test slide 18 then placed in the slide holder 16 with the coated or oil-absorbent surface of the slide toward the fitting 20 containing the orifice 24 so that the air sample 26 will impinge on the coated surface of the test slide essentially perpendicular to the slide surface. The line pressure is then observed and recorded on the pressure gauge 14 and then the valve 22 opened for a defined time period, for example, 1 to 5 minutes. Where the compressed air has a low amount of oil mist, for example, if oil-mist filters are installed in the air line; that is, the air is essentially clean air, it may be necessary to leave the valve open for greater periods of time. After the defined time period, the valve 22 is closed and the slide 18 removed from the holder 16. The test slide 18 is then placed under a source of ultraviolet light and compared with a standard plate to determine the amoun of oil concentration.

FIG. 3 is an illustration in comparison of a test plate and a standard plate wherein the standard plate contains a series or typically different diameter spots showing increasing oil-mist concentration in the compressed air. The oil mist on the test slide may be identified as to the concentration range by a comparison between the darkened spot on the test plate in comparison to the darkened spots on the standard plate. This provides a semiquantitative determination of the amount of the oil mist in the compressed air. The standard plate can be marked if desired adjacent each area or spot in parts per million of oil mist represented under the defined test conditions for that spot. At lower concentration levels where there is not much difference in the diameter of the test spots, the determination may be made through the degrees of intensity of fluorescent quenching of the darkened area on the test plate compared to the fluorescent quenching on the standard plate or a combination of spot diameter and the degree of fluorescent quenching.

The test apparatus of FIGS. 1 and 2 was installed on a ½-inch compressed-air line, the air line containing in series; a lubricator to supply oil mist, a trap, such as a type 92 Balston filter housing without the filter tube which would capture gross oil-liquid droplets not in aerosol form in the bowl of the trap, the test apparatus and a flow meter with a valve. Tests were carried out with both standard no. 2 compressor oil and a synthetic diester oil as contaminants representing the oil mist. The No. 2 oil and diester were tested separately with line pressure of the compressed air line regulated to 100 psig with a 400 standard cubic feet per hour flow being observed.

A silica gel chromatography slide containing a UV-254 NPT phosphor indicator was placed in the slide holder. The valve on the test apparatus was then opened for a period of one minute and closed. The test slide was then removed and examined under 254 NM ultraviolet light. In both test cases the results showed a dark spot had appeared on the test slide where the oil impingement had occurred. The darkness was a result of fluorescent quenching of the phosphor indicator on the chromatography test slide. A nonwoven glass-fiber bonded filter tube was then installed in the filter tube housing and the tests repeated with the results that the quenching of each test contaminant was smaller and less intense in color than without the filter, which indicated that the tests were semiquantitative in nature.

A standard test plate may be prepared under the same test conditions by inserting a test slide into the test holder and exposing each portion of the plate to different defined time periods to obtain, for example, a standard plate of 0, 1, 5, 10, 30, 50 and 100 parts per million of oil mist as a standard plate. The standard plate may be prepared for lower concentrations, such as 0.1 to 5 parts per millions, by exposure for longer periods of time to show the difference in the degree of darkening or quenching.

My test method and test apparatus have been described in particular in connection with the determination of oil mist in compressed air or air under pressure. However, it is recognized that my test method and apparatus may be used to determine generally contaminants in any source of compressed gas wherein the contaminant serves to quench the UV indicator in the test plate, such as for example, testing for various hydrocarbon mist or chemical-mists in other compressed gases.

What I claim is:

1. A method of determining the amount of oil mist in a compressed-air stream, which method comprises:
   (a) bleeding a small sample of compressed air from the compressed-air line through a bleed orifice of predetermined dimensions for a defined bleed-time period at a known pressure;
   (b) directly impinging the bleed-air sample in a substantially perpendicular direction onto the surface of a plate spaced apart a predetermined distance from the orifice, the plate containing an ultraviolet phosphor indicator, which phosphor indicator is inhibited in fluorescence by the oil mist in the compressed-air sample;
   (c) comparing the coated plate on which the bleed-air sample has been impinged with a standard plate under ultraviolet radiation sufficient to fluoresce the ultraviolet phosphor indicator; and
   (d) determining from such comparison of said plates the amount of oil mist present in the compressed-air stream.

2. The method of claim 1 wherein the plate is a silica-coated plate containing an ultraviolet phosphor indicator in the coating of the plate.

3. The method of claim 1 which includes bleeding a compressed-air sample from a compressed-air line through an orifice of about 0.010 to 0.020 inches for a time period of about 10 seconds to 5 minutes at a pressure range of from about 80 to 120 psig.

4. The method of claim 1 wherein the standard plate comprises a series of oil spots on the surface thereof of different dimensions as an indication of known concentration of oil mist through which the plate exposed to the bleed sample is compared.

5. The method of claim 1 wherein the comparison includes comparing the amount of darkening under ultraviolet light of the area on the plate on which the bleed sample is impinged with the darkness of the areas of the standard plate under ultraviolet light to determine the amount of oil-mist concentration in the bleed-air sample.

6. The method of claim 1 which includes the step of selecting a nonwoven, bonded, glass-fiber filter to be employed in the compressed-air stream based on the determination of the amount of oil mist in the compressed-air stream as tested.

7. The method of claim 1 wherein the plate is spaced apart from the orifice and directly perpendicular thereto for a distance of between 0.125" to 2 inches.

8. The method of claim 2 wherein the standard plate comprises a plate coated with an oil-absorbent coating containing a phosphor indicator and has a plurality of standard, generally circular areas of different dimensions.

9. The method of claim 1 which includes comparing the sample plate with the standard plate containing a number of different standard oil areas thereon and determining the amount of oil mist based on the darkness area on the standard to the size of the darkness area of the test area.

10. A method of determining the amount of oil mist in a compressed-air stream, which method comprises:
   (a) bleeding a small sample of compressed air from the compressed-air line through a bleed orifice of about 0.010 to 0.020 inches for a bleed-time period of about 10 seconds to 5 minutes at a pressure range of from about 80 to 120 psig;
   (b) directly impinging the bleed-air sample in a substantially perpendicular direction onto the surface of a plate spaced apart at a predetermined distance from the orifice, the plate containing an ultraviolet phosphor indicator, which phosphor indicator is inhibited in fluorescence by the oil mist in the compressed-air sample;
   (c) comparing the silica-coated plate on which the bleed-air sample has been impinged with a standard plate under ultraviolet radiation sufficient to fluoresce the ultraviolet phosphor indicator; and
   (d) determining from such comparison of said plates the amount of oil mist present in the compressed-air stream.

11. A standard plate adapted to be used in determining the amount of oil mist in a compressed-air sample, which plate comprises:
   a plate containing an oil-absorbent coating thereon and the coating containing an ultraviolet phosphor indicator which under ultraviolet light is inhibited in fluroescence by oil mist, the plate characterized by a plurality of separate oil-mist area thereon of known concentration and varying area size whereby a sample plate with an oil-mist area thereon may be compared with the standard plate to determine the amount of oil mist on the sample plate.

12. The plate of claim 11 wherein the plate is a glass plate coated with silica and having an indicator which fluoresces at about 2540 Angstroms.

13. A test-kit apparatus for determining the amount of oil mist in a compressed-air stream, which test kit comprises in combination:
   (a) a standard fitting adapted for insertion in the compressed-air line from which a compressed-air sample is to be bled;
   (b) a pressure gauge to determine the amount of pressure of the compressed-air stream;
   (c) a fitting containing an orifice of defined dimensions in the fitting;
   (d) a valve means to introduce and control the compressed air bled from the compressed-air line to the orifice;
   (e) a plate-holder meand to secure a test plate in a direction a predetermined distance from and its surface substantially perpendicular to the defined orifice;
   (f) a test plate adapted to be inserted in the test plate holder, the test plate comprising an oil-absorbent plate containing an ultraviolet phosphor indicator; and
   (g) a standard plate similar to the test plate, the standard test plate containing thereon a plurality of known oil-mist samples at known concentration levels whereby on directly impinging a compressed-air sample containing oil mist onto the test plate in the test holder for a defined period of time, the test plate may be compared under ultraviolet radiation with the standard plate to determine the amount of oil mist in the compressed-air line.

14. The kit apparatus of claim 13 wherein the test plate holder comprises a glass slide containing an oil-absorbent, silica coating thereon, the coating containing an ultraviolet phosphor indicator.

15. The method of claim 1 wherein the bleed time period ranges from 30 seconds to 10 minutes.

16. The method of claim 1 wherein the known pressure ranges from about 80 to 125 psig.

17. The method of claim 1 wherein the oil mist in the compressed air stream has a particle size of less than about 5 microns.

18. The method of claim 1 which includes comparing the coated plate with a standard plate having known oil-spot standards ranging from 0 to 100 ppm.

19. The kit apparatus of claim 13 wherein the orifice has a diameter of about 0.010 to 0.020 inches.

20. The kit apparatus of claim 13 wherein the standard plate comprises a plate coated with an oil-absorbent coating containing a phosphor indicator and has a plurality of standard, generally circular areas of different dimensions.

21. The plate of claim 11 wherein the standard plate comprises a plurality of generally circular standard areas of varying size representing known oil-mist concentration of from about 0 to 100 ppm.

* * * * *